US009050369B2

(12) United States Patent
Nakata et al.

(10) Patent No.: US 9,050,369 B2
(45) Date of Patent: Jun. 9, 2015

(54) AQUEOUS OPHTHALMIC COMPOSITION

(71) Applicant: ROHTO PHARMACEUTICAL CO., LTD., Osaka (JP)

(72) Inventors: Atsuko Nakata, Osaka (JP); Eri Matsumoto, Osaka (JP)

(73) Assignee: ROHTO PHARMACEUTICAL CO., LTD., Osaka (JP)

( * ) Notice: Subject to any disclaimer, the term of this patent is extended or adjusted under 35 U.S.C. 154(b) by 65 days.

(21) Appl. No.: 13/720,734

(22) Filed: Dec. 19, 2012

(65) Prior Publication Data

US 2014/0005277 A1 Jan. 2, 2014

Related U.S. Application Data

(60) Provisional application No. 61/667,661, filed on Jul. 3, 2012.

(30) Foreign Application Priority Data

Jun. 27, 2012 (JP) ................................ 2012-144221

(51) Int. Cl.
A61K 47/44 (2006.01)
A61K 9/00 (2006.01)

(52) U.S. Cl.
CPC .............. A61K 47/44 (2013.01); A61K 9/0048 (2013.01)

(58) Field of Classification Search
CPC ............................ A61K 47/44; A61K 9/0048
USPC ................................................. 514/769, 783
See application file for complete search history.

(56) References Cited

U.S. PATENT DOCUMENTS

| | | | | |
|---|---|---|---|---|
| 6,348,508 | B1 * | 2/2002 | Denick et al. ............... | 514/772.4 |
| 2007/0053861 | A1 | 3/2007 | Nakayama et al. | |
| 2008/0194532 | A1 * | 8/2008 | Rabinovich-Guilatt et al. ................. | 514/182 |
| 2010/0305046 | A1 | 12/2010 | Yu | |
| 2013/0296446 | A1 * | 11/2013 | Furumiya et al. ............. | 514/783 |

FOREIGN PATENT DOCUMENTS

| | | |
|---|---|---|
| CN | 102028697 | 4/2011 |
| EP | 1889620 | 2/2008 |
| JP | 2000-159659 | 6/2000 |
| JP | 2000-273061 | 10/2000 |
| JP | 2002-356420 | 12/2002 |
| JP | 2005-206598 | 8/2005 |
| JP | 2005-298448 | 10/2005 |
| JP | 2006-117656 | 5/2006 |
| JP | 2009-173638 | 8/2009 |
| JP | 2011-068683 | 4/2011 |
| JP | 2012-144527 | 8/2012 |
| TW | 201024320 | 7/2010 |
| WO | 2005/025539 | 3/2005 |
| WO | 2010/064636 | 6/2010 |
| WO | 2011/001951 | 1/2011 |

OTHER PUBLICATIONS

International Preliminary Report on Patentability and Written Opinion dated Jan. 23, 2014 for PCT/JP2012/067194.
International Preliminary Report on Patentability and Written Opinion dated Jan. 23, 2014 for PCT/JP2012/067193.
International Preliminary Report on Patentability and Written Opinion dated Jan. 23, 2014 for PCT/JP2012/067195.
Matsumura, Y. et al., Composition useful as otorhinological agent and ophthalmic composition, comprises cellulose thickening agents, nonionic surfactant and castor oil, Database WPI, Section Ch, Week 201129, Thomson Scientific, London, GB, AN 2011-D57885, Apr. 7, 2011, p. 13, XP002732933.
Chen, J. et al., Novel culturing method for *Antrodia camphorata* mycelium—replaces the conventional chemical defoaming agent by adding sesame oil in the *Antrodia camphorate* culturing medium, Database WPI, Section Ch, Week 201156, Thomson Scientific, London, GB, AN 2011-D67308, Jul. 1, 2010, XP002732934.
Saleem, T.S.M., Anti-microbial activity of sesame oil, Int. J. Res. Phytochem. Pharmacol., vol. 1, No. 1, Jan. 2011-Mar. 2011, pp. 21-23, XP002732935.
Teressa, S. et al., Ultra Violet Transmission Through a Few Edible Oils in the Context of Changing Solar Insolation, J. Ind. Geophys. Union, vol. 8, No. 4, Oct. 2004, pp. 267-271, XP002732936.
Prasad, N.R. et al., Photoprotective effect of sesamol on UVB-radiation induced oxidative stress in human blood lymphocytes in vitro, Environmental Toxicology and Pharmacology, Elsevier, Amsterdam, NL, vol. 20, No. 1, Jul. 1, 2005, pp. 1-5, XP027640610.
Kurumada, T., Aqueous liquid agent, useful in ophthalmic preparation e.g. eye drops, contains azulene, berberine, buffer and non-ionic surfactant as main components, Database WPI, Section Ch, Week 200580, Thomson Scientific, London, GB, AN 2005-773502, XP002732937.
Tamilvanan, S. et al., The potential of lipid emulsion for ocular delivery of lipophilic drugs, European Journal of Pharmaceutics and Biopharmaceutics, Elsevier Science Publishers B.V., Amsterdam, NL, vol. 58, No. 2, Sep. 1, 2004, pp. 357368, XP004526318.
Office Action dated Oct. 8, 2014 for U.S. Appl. No. 14/130,709.
Chinese Office Action, dated Jan. 28, 2015, in corresponding CN Patent Application No. 201280032892.2.

* cited by examiner

*Primary Examiner* — Sean Basquill
(74) *Attorney, Agent, or Firm* — Roylance, Abrams, Berdo & Goodman, L.L.P.

(57) ABSTRACT

This invention relates to an aqueous ophthalmic composition comprising (A) polyoxyethylene castor oil and (B) sesame oil. According to the aqueous ophthalmic composition of the present invention, defoaming time is reduced, preservative efficacy is enhanced and photostability is improved.

5 Claims, No Drawings

AQUEOUS OPHTHALMIC COMPOSITION

BACKGROUND OF THE INVENTION

1. Technical Field

The present invention relates to an aqueous ophthalmic composition. More specifically, the present invention relates to an aqueous ophthalmic composition having a reduced defoaming time, enhanced preservative efficacy, and improved photostability.

2. Background Art

In the field of ophthalmology, solubilizing agents are added to a variety of preparations. In particular, in aqueous ophthalmic compositions, various solubilizing agents are added for the purpose of helping dissolution of biologically active components and additives with relatively low water solubility, and the like. A surfactant can be given as an example of the solubilizing agents used in the field of ophthalmology. It is known that polyoxyethylene castor oil is a nonionic surfactant and is added to an aqueous ophthalmic composition to help dissolve other components (JP2005-298448A).

An aqueous composition containing a surfactant is known to easily foam, and foam is generated when vibration or impact is applied during production or distribution. In general, to use the aqueous ophthalmic composition in a manner safe on the eyes, the dissolution check during production is considered important. Of aqueous ophthalmic compositions, medical products such as eye drops and eye washes require foreign matter detection in the production steps. However, when foam is generated in the aqueous ophthalmic composition during production, and disappears at low speed, it is hard to distinguish active ingredients or foreign matter from the foam. Consequently, steps such as dissolution check and foreign matter detection take a long period of time, which prevents efficient production.

Further, it is desirable that an aqueous ophthalmic composition prevents a product from spoiling due to microbial contamination or the like during use. Therefore, an antiseptic is added to each aqueous composition for the purpose of preventing spoiling to ensure preservation stability of the aqueous composition. However, in general, nonionic surfactants are known to have an effect of inactivating antiseptics to reduce antiseptic action. Accordingly, preservative efficacy in a composition containing a nonionic surfactant is predicted to be insufficient.

Moreover, it is important for aqueous compositions to ensure stability during production and market circulation, and long-term stability after opening. Therefore, an adverse effect on quality by the decomposition of components due to light exposure cannot be ignored. Hence, a method for stably preserving a solution for a long period of time while preventing photodecomposition is desired.

On the other hand, to improve the properties of aqueous ophthalmic compositions, addition of vegetable oil has been attempted. For example, as a method for stabilizing the viscosity of a composition, JP2006-117656A discloses a sesame oil-containing composition that is applicable to mucous membranes.

However, effects on the defoaming time, preservative efficacy, and photostability attained by adding sesame oil to an aqueous ophthalmic composition have not yet been clarified. In particular, an effect on an aqueous ophthalmic composition provided when these components and a specific surfactant are added to the aqueous ophthalmic composition cannot be easily predicted.

SUMMARY OF THE INVENTION

Because of the importance of steps such as dissolution check and foreign matter detection in the aqueous ophthalmic composition described above, reducing the defoaming time is an important object of the aqueous ophthalmic composition. The present invention was made in light of such prior art and provides an aqueous ophthalmic composition having a reduced defoaming time when foam is generated by vibration or impact, wherein the aqueous ophthalmic composition is an aqueous ophthalmic composition that easily generates foam due to inclusion of a solubilizing agent such as a surfactant. The present invention also provides a method for reducing the defoaming time in the aqueous ophthalmic composition.

Another object of the present invention is to provide a specific nonionic surfactant-containing aqueous ophthalmic composition that has enhanced preservative efficacy for a long period of time regardless whether an antiseptic is added to impart an antiseptic effect; and a further object is to provide a method for enhancing preservative efficacy in the aqueous ophthalmic composition.

Furthermore, the research of the present inventors confirms that, of the components contained in the aqueous ophthalmic composition of the present invention described below, polyoxyethylene castor oil is likely to become decomposed when it is exposed to light. Since the photodecomposition of the components in the aqueous ophthalmic composition causes reduction in commercial product value and in quality including safety, and further prevents the components from exhibiting properties that the components originally have, improving photostability is an extremely important object.

Accordingly, another object of the present invention is to provide an aqueous ophthalmic composition having improved photostability and to provide a method for improving stability in the aqueous ophthalmic composition.

To achieve the above objects, the present inventors conducted extensive research. As a result, they found the following. When foam is generated by vibration or impact, the defoaming time is significantly reduced by adding sesame oil (hereinafter sometimes referred to as "component (B)") to an aqueous ophthalmic composition containing, as a non-ionic surfactant, polyoxyethylene castor oil (hereinafter sometimes simply referred to as "component (A)"). This makes it possible to perform dissolution check and foreign matter detection in a short period of time. Further, an aqueous ophthalmic composition such as eye drops in which foam is generated shows large variation in the drip amount per use. In particular, for eye drops or solutions for wearing a contact lens used in a relatively small amount each time, users have difficulty in controlling the amount used per use, thus causing disadvantages such as difficulty in handling. In particular, when the aqueous ophthalmic composition is used as a medical product, compliance may be reduced. The present invention, however, can reduce the defoaming time; therefore, variation in the drip amount of the aqueous ophthalmic composition can also be reduced.

Research of the present inventors also reveals that an aqueous ophthalmic composition containing polyoxyethylene castor oil and sesame oil in combination has enhanced preservative efficacy. Generally, nonionic surfactants are known to have an effect of inactivating antiseptics to reduce antiseptic action. Accordingly, the fact that preservative efficacy is enhanced when polyoxyethylene castor oil, which is a nonionic surfactant, is used in combination with sesame oil is a completely unexpected effect.

Further research of the present inventors reveals that, by adding sesame oil to an aqueous ophthalmic composition containing polyoxyethylene castor oil, the photodecomposition of polyoxyethylene castor oil in the aqueous ophthalmic composition is inhibited, thereby improving photostability.

The present invention was accomplished as a result of further research based on these findings.

Accordingly, the present invention provides aqueous ophthalmic compositions according to the following embodiments.

Item 1-1. An aqueous ophthalmic composition comprising (A) polyoxyethylene castor oil and (B) sesame oil.

Item 1-2. The aqueous ophthalmic composition according to Item 1-1, wherein component (A) is polyoxyethylene castor oil in which the average number of moles of added ethylene oxide is 2 to 70.

Item 1-3. The aqueous ophthalmic composition according to Item 1-1 or 1-2, wherein component (A) is polyoxyethylene castor oil in which the average number of moles of added ethylene oxide is 2 to 35.

Item 1-4. The aqueous ophthalmic composition according to any one of Item 1-1 to Item 1-3, wherein the total content of component (A) is 0.0005 to 5 w/v % based on the total amount of the aqueous ophthalmic composition.

Item 1-5. The aqueous ophthalmic composition according to any one of Items 1-1 to 1-4, wherein the total content of component (B) is 0.0001 to 5 w/v % based on the total amount of the aqueous ophthalmic composition.

Item 1-6. The aqueous ophthalmic composition according to any one of Items 1-1 to 1-5, wherein the total content of component (B) is 0.00002 to 10,000 parts by weight relative to 1 part by weight of the total content of component (A).

Item 1-7. The aqueous ophthalmic composition according to any one of Items 1-1 to 1-6, wherein the total content of component (B) is 0.005 to 10 parts by weight relative to 1 part by weight of the total content of component (A).

Item 1-8. The aqueous ophthalmic composition according to any one of Items 1-1 to 1-7, which further comprises at least one member (hereinbelow sometimes referred to as "component (C)") selected from the group consisting of boric acids and salts thereof.

Item 1-9. The aqueous ophthalmic composition according to Item 1-8, wherein the total content of component (C) is 0.01 to 10 w/v % based on the total amount of the aqueous ophthalmic composition.

Item 1-10. The aqueous ophthalmic composition according to any one of Items 1-1 to 1-9, which further comprises a buffer.

Item 1-11. The aqueous ophthalmic composition according to any one of Items 1-1 to 1-10, which further comprises a nonionic surfactant other than component (A).

Item 1-12. The aqueous ophthalmic composition according to Item 1-11, wherein the nonionic surfactant other than component (A) is at least one member selected from the group consisting of polyoxyethylene sorbitan fatty acid esters, polyoxyethylene hydrogenated castor oils, and polyoxyethylene-polyoxypropylene block copolymers.

Item 1-13. The aqueous ophthalmic composition according to Item 1-11 or 1-12, wherein the total content of the nonionic surfactant other than component (A) is 0.001 to 3 w/v % based on the total amount of the aqueous ophthalmic composition.

Item 1-14. The aqueous ophthalmic composition according to any one of Items 1-1 to 1-13, which further comprises polyhydric alcohol.

Item 1-15. The aqueous ophthalmic composition according to Item 1-14, wherein the polyhydric alcohol is at least one member selected from the group consisting of glycerin, propylene glycol, polyethylene glycol, mannitol, and sorbitol.

Item 1-16. The aqueous ophthalmic composition according to Item 1-14 or 1-15, wherein the total content of the polyhydric alcohol is 0.005 to 10 w/v % based on the total amount of the aqueous ophthalmic composition.

Item 1-17. The aqueous ophthalmic composition according to any one of Items 1-1 to 1-16, which is placed in a polyethylene terephthalate container.

Item 1-18. The aqueous ophthalmic composition according to any one of Items 1-1 to 1-17, which is placed in a container on which a polyethylene nozzle is mounted.

Item 1-19. The aqueous ophthalmic composition according to any one of Items 1-1 to 1-18, which is eye drops.

Item 1-20. The aqueous ophthalmic composition according to any one of Items 1-1 to 1-18, which is an eye wash.

Item 1-21. The aqueous ophthalmic composition according to any one of Items 1-1 to 1-18, which is a solution for wearing a contact lens.

Item 1-22. The aqueous ophthalmic composition according to any one of Items 1-1 to 1-18, which is a contact lens care solution.

The present invention also provides methods for reducing the defoaming time in an aqueous ophthalmic composition and a method for reducing variation in the drip amount during use according to the following embodiments.

Item 2. A method for reducing defoaming time in an aqueous ophthalmic composition, comprising adding (A) polyoxyethylene castor oil and (B) sesame oil to the aqueous ophthalmic composition.

Item 3. A method for reducing defoaming time in an aqueous ophthalmic composition, comprising adding (B) sesame oil to the aqueous ophthalmic composition containing (A) polyoxyethylene castor oil.

Item 4. A method for reducing variation in drip amount during use in an aqueous ophthalmic composition, comprising adding (A) polyoxyethylene castor oil and (B) sesame oil to the aqueous ophthalmic composition.

The present invention provides a method for enhancing preservative efficacy in an aqueous ophthalmic composition according to the following embodiment.

Item 5. A method for enhancing preservative efficacy in an aqueous ophthalmic composition, comprising adding (A) polyoxyethylene castor oil and (B) sesame oil to the aqueous ophthalmic composition.

Further, the present invention provides methods for improving photostability in an aqueous ophthalmic composition according to the following embodiments.

Item 6. A method for improving photostability in an aqueous ophthalmic composition, comprising adding (B) sesame oil to the aqueous ophthalmic composition containing (A) polyoxyethylene castor oil.

Item 7. A method for improving photostability in an aqueous ophthalmic composition, comprising adding (A) polyoxyethylene castor oil and (B) sesame oil to the aqueous ophthalmic composition.

Furthermore, the present invention provides use according to the following embodiments.

Item 8. Use of (A) polyoxyethylene castor oil and (B) sesame oil for production of an aqueous ophthalmic composition.

Item 9. The use according to Item 8, wherein the aqueous ophthalmic composition is the composition according to any one of Items 1-1 to 1-22.

The present invention also provides use according to the following embodiments.

Item 10. Use of a composition as an aqueous ophthalmic composition, the composition comprising (A) polyoxyethylene castor oil and (B) sesame oil.

Item 11. The use according to Item 10, wherein the composition is the composition according to any one of Items 1-1 to 1-22.

Still further, the present invention provides compositions according to the following embodiments.

Item 12. A composition for use as an aqueous ophthalmic composition, the composition comprising (A) polyoxyethylene castor oil and (B) sesame oil.

Item 13. The composition according to Item 12, which is recited in any one of Items 1-1 to 1-22.

The present invention provides methods for producing an aqueous ophthalmic composition according to the following embodiments.

Item 14. A method for producing an aqueous ophthalmic composition, comprising adding (A) polyoxyethylene castor oil and (B) sesame oil to a carrier containing water.

Item 15. The method according to Item 14, wherein the aqueous ophthalmic composition is the composition according to any one of Items 1-1 to 1-22.

Advantageous Effects of Invention

The present invention can attain the following various effects.

(1) According to the present invention, the defoaming time in the aqueous ophthalmic composition containing polyoxyethylene castor oil can be reduced. As a result, dissolution check or foreign matter detection during the production of the aqueous ophthalmic composition can be performed in a short period of time, and thus the production efficiency can be improved. Further, variation in the amount of drip can be reduced by shortening the defoaming time.

(2) The aqueous ophthalmic composition of the present invention has enhanced preservative efficacy. Therefore, in the field of ophthalmology, which requires particularly high level of safety against bacterial contamination, contamination of the aqueous ophthalmic composition during use, microorganism infection risk, etc., can be reduced.

(3) According to the present invention, it is possible to inhibit photodecomposition of polyoxyethylene castor oil, which is likely to occur when the composition is exposed to light, in a polyoxyethylene castor oil-containing aqueous ophthalmic composition. Accordingly, the aqueous ophthalmic composition of the present invention can stably exhibit excellent properties of polyoxyethylene castor oil for a long period of time without impairing safety and quality.

The aqueous ophthalmic composition of the present invention has the aforementioned excellent effects and can be effectively used for a long period of time in a safer and more comfortable manner.

DESCRIPTION OF EMBODIMENTS

In the present specification, the unit of content "%" indicates w/v % and is same as g/100 mL.

In the present specification, the abbreviation "POE" means polyoxyethylene unless otherwise specified.

In the present specification, the abbreviation "POP" means polyoxypropylene unless otherwise specified.

In the present specification, contact lenses include all kinds of contact lenses including hard lenses, oxygen-permeable hard lenses, soft lenses (including silicone hydrogel lenses), and color lenses unless otherwise specified.

The present invention is explained in detail below.

1. Aqueous Ophthalmic Composition

The aqueous ophthalmic composition of the present invention contains polyoxyethylene castor oil (component (A)). By using the polyoxyethylene castor oil in combination with sesame oil described below, the present invention can attain the aforementioned excellent effects.

Polyoxyethylene castor oil is a known compound obtained by addition polymerization of ethylene oxide with castor oil, and several kinds of polyoxyethylene castor oils having a different average number of moles of added ethylene oxide are known. In the present invention, the average number of moles of added ethylene oxide in the polyoxyethylene castor oil used as component (A) is not particularly limited. For example, the average number of moles of added ethylene oxide is about 2 to 70. Specific examples include polyoxyethylene castor oil 3 in which the average number of moles of added ethylene oxide is 3, polyoxyethylene castor oil 4 in which the average number of moles of added ethylene oxide is 4, polyoxyethylene castor oil 6 in which the average number of moles of added ethylene oxide is 6, polyoxyethylene castor oil 7 in which the average number of moles of added ethylene oxide is 7, polyoxyethylene castor oil 10 in which the average number of moles of added ethylene oxide is 10, polyoxyethylene castor oil 13.5 in which the average number of moles of added ethylene oxide is 13.5, polyoxyethylene castor oil 17 in which the average number of moles of added ethylene oxide is 17, polyoxyethylene castor oil 20 in which the average number of moles of added ethylene oxide is 20, polyoxyethylene castor oil 25 in which the average number of moles of added ethylene oxide is 25, polyoxyethylene castor oil 30 in which the average number of moles of added ethylene oxide is 30, polyoxyethylene castor oil 35 in which the average number of moles of added ethylene oxide is 35, polyoxyethylene castor oil 40 in which the average number of moles of added ethylene oxide is 40, polyoxyethylene castor oil 50 in which the average number of moles of added ethylene oxide is 50, polyoxyethylene castor oil 60 in which the average number of moles of added ethylene oxide is 60, and polyoxyethylene castor oil 70 in which the average number of moles of added ethylene oxide is 70.

Of these, polyoxyethylene castor oil in which the average number of moles of added ethylene oxide is 2 to 35, preferably 2 to 30, more preferably 2 to 20, and particularly preferably 2 to 12, is an example of the polyoxyethylene castor oils that suitably exhibit effects of the present invention.

In the present invention, these polyoxyethylene castor oils may be used singly or in any combination of two or more. Note that polyoxyethylene castor oil used in the present invention is a compound that is different from and can be distinguished from polyoxyethylene hydrogenated castor oil obtained by addition polymerization of hydrogenated castor oil with ethylene oxide.

The content of component (A) in the aqueous ophthalmic composition of the present invention is not particularly limited and is suitably determined according to the kind of component (A), kind and content of component (B) used in combination with component (A), and the application, preparation form, usage, etc. of the aqueous ophthalmic composition. For example, the total content of component (A) is 0.0005 to 5 w/v %, preferably 0.001 to 4 w/v %, more preferably 0.002 to 3 w/v %, even more preferably 0.005 to 2, and particularly preferably 0.01 to 1 w/v % based on the total amount of the aqueous ophthalmic composition of the present invention.

The aforementioned content of component (A) is preferable to further improve the effect of reducing the defoaming time, the effect of enhancing preservative efficacy, and the effect of improving photostability in the aqueous ophthalmic composition.

It is necessary for the aqueous ophthalmic composition of the present invention to include sesame oil (component (B)) in addition to component (A). Thus, by the combined use of component (A) and component (B), the aforementioned effects, i.e., the effect of reducing the defoaming time, effect of enhancing preservative efficacy, and effect of improving photostability can be exhibited.

Sesame oil means a vegetable oil obtained from seeds of plants belonging to the genus *sesamum* of the family Pedaliaceae, e.g., *Sesamumindicum Linne* (Pedaliaceae).

Sesame oil used in the present invention is not particularly limited as long as it is a pharmacologically (pharmaceutically) or physiologically acceptable oil in the field of medicine. Sesame oil obtained from seeds by using a known exploitation method or known purification method, or commercially available oil can be used.

The content of component (B) in the aqueous ophthalmic composition of the present invention is not particularly limited and can be suitably determined according to the kind and content of component (A) used in combination with component (B), and the application, preparation form, usage, etc. of the aqueous ophthalmic composition. For example, the total content of component (B) is 0.0001 to 5 w/v %, preferably 0.0005 to 1 w/v %, more preferably 0.001 to 0.5 w/v %, and particularly preferably 0.005 to 0.1 w/v % based on the total amount of the aqueous ophthalmic composition of the present invention.

The aforementioned content of component (B) is preferable to further improve the effect of the present invention.

The content ratio of component (B) to component (A) in the aqueous ophthalmic composition of the present invention is not particularly limited and is suitably determined according to the kinds of components (A) and (B), and the application, preparation form, usage, etc., of the aqueous ophthalmic composition. For example, the total content of component (B) is 0.00002 to 10,000 parts by weight, preferably 0.0001 to 1,000 parts by weight, more preferably 0.0005 to 200 parts by weight, even more preferably 0.002 to 50 parts by weight, and particularly preferably 0.005 to 10 parts by weight relative to 1 part by weight of the total content of component (A) contained in the aqueous ophthalmic composition of the present invention.

The aforementioned content ratio of component (B) to component (A) is preferable in view of further improvement of the effect of the present invention.

As described below, various pharmacologically active components, biologically active components, etc., can be added, according to the purpose of use, to the aqueous ophthalmic composition of the present invention, and various kinds of additives can also be added. In this case, to improve the solubility of biologically active components, additives, etc., a surfactant other than component (A) can be added as a solubilizing agent. In general, the addition of such a surfactant increases foaming; however, according to the present invention, the defoaming time in an aqueous ophthalmic composition that is likely to make foam due to the addition of a surfactant other than component (A) can also be reduced by concurrently adding component (A) and component (B). The production efficiency can also be improved, and further, variation in the drip amount can be reduced.

The surfactant other than component (A), which can be added to the aqueous ophthalmic composition of the present invention, is not particularly limited as long as it is a pharmacologically (pharmaceutically) or physiologically acceptable surfactant in the field of medicine. The surfactant may be a nonionic surfactant, ampholytic surfactant, anionic surfactant, or cationic surfactant.

Specific examples of the nonionic surfactant other than component (A) that can be added to the aqueous ophthalmic composition of the present invention include POE (20) sorbitan monolaurate (polysorbate 20), POE (20) sorbitan monopalmitate (polysorbate 40), POE (20) sorbitan monostearate (polysorbate 60), POE (20) sorbitan tristearate (polysorbate 65), and POE (20) sorbitan monooleate (polysorbate 80), and like POE sorbitan fatty acid esters; POE (40) hydrogenated castor oil (polyoxyethylene hydrogenated castor oil 40), POE (60) hydrogenated castor oil (polyoxyethylene hydrogenated castor oil 60), and like POE hydrogenated castor oils; POE (9) lauryl ether, and like POE alkyl ethers; POE (20) POP(4) cetyl ether, and like POE-POP alkyl ethers; POE (196) POP (67) glycol (poloxamer 407, pluronic F127), POE (200) POP (70) glycol, and like polyoxyethylene-polyoxypropylene block copolymers. In the compounds listed above, each of the numbers in the parentheses shows the number of moles of the added compounds.

Specific examples of the ampholytic surfactant that can be added to the aqueous ophthalmic composition of the present invention include alkyldiaminoethylglycine or salts thereof (e.g. hydrochloride).

Specific examples of the cationic surfactant that can be added to the aqueous ophthalmic composition of the present invention include benzalkonium chloride, benzethonium chloride, and the like.

Specific examples of the anionic surfactant that can be added to the aqueous ophthalmic composition of the present invention include alkylbenzene sulfonate, alkyl sulfate, polyoxyethylene alkyl sulfate, aliphatic α-sulfomethyl ester, α-olefin sulfonic acid, and the like.

A preferable examples of the surfactant other than component (A), which can be added to the aqueous ophthalmic composition of the present invention, include nonionic surfactants other than component (A), more preferably POE sorbitan fatty acid esters, POE hydrogenated castor oils, and POE-POP block copolymers, and particularly preferably polysorbate 80, polyoxyethylene hydrogenated castor oil 60, and poloxamer 407.

In the aqueous ophthalmic composition of the present invention, the surfactants other than component (A) can be used singly or in a combination of two or more.

When a surfactant other than component (A) is added to the aqueous ophthalmic composition of the present invention, the content thereof is suitably determined according to the kind of the surfactant, kinds and contents of other components, and the application, preparation form, usage, etc. of the aqueous ophthalmic composition. For example, the total content of the surfactant other than component (A) is 0.001 to 3 w/v %, preferably 0.005 to 2 w/v %, more preferably 0.01 to 1 w/v %, and particularly preferably 0.05 to 1 w/v %, based on the total amount of the aqueous ophthalmic composition of the present invention.

The aqueous ophthalmic composition of the present invention preferably includes at least one member (component (C)) selected from the group consisting of boric acids and salts thereof. By including at least one member selected from the group consisting of boric acids and salts thereof, the effect of the present invention can be further improved.

Boric acid collectively refers to oxoacid generated by hydration of diboron trioxide, and examples thereof include orthoboric acid, metaboric acid, tetra boric acid, and the like. Boric acid is a known compound and may be synthesized by a known method or can be obtained as a commercially available product.

Examples of salts of boric acid include boric acid salts such as alkali metal salt of boric acid and alkaline earth metal salt of boric acid. As a boric acid salt, a hydrate of boric acid salt can also be used. Specific examples of component (C) include boric acid (orthoboric acid), sodium borate, potassium tetraborate, potassium metaborate, ammonium borate, borax, and the like. The boric acids and salts thereof can be used singly or in a combination of two or more. Preferable examples of component (C) include a combination of boric acid and salt thereof, more preferably a combination of boric acid and alkali metal salt of boric acid and/or alkaline earth metal salt of boric acid, even more preferably a combination of boric acid and alkali metal salt of boric acid, and particularly preferably a combination of boric acid and borax.

In the aqueous ophthalmic composition of the present invention, the content of component (C) is not particularly limited and can be suitably determined according to the kind of component (C), kinds and contents of other components, and the application, preparation form, usage, etc. of the aqueous ophthalmic composition. For example, based on the total amount of the aqueous ophthalmic composition of the present invention, the total content of component (C) is 0.01 to 10 w/v %, preferably 0.05 to 5 w/v %, more preferably 0.1 to 3 w/v %, and particularly preferably 0.2 to 2 w/v %.

The aqueous ophthalmic composition of the present invention can further include a buffer. Thereby, the pH of the aqueous ophthalmic composition of the present invention can be adjusted. A buffer that can be added to the aqueous ophthalmic composition of the present invention is not particularly limited as long as it is a pharmacologically (pharmaceutically) or physiologically acceptable buffer in the field of medicine. Examples of such a buffer include phosphoric acid buffers, carbonic acid buffers, citric acid buffers, acetic acid buffers, tris buffers, aspartic acids, aspartic acid salts, epsilon-aminocaproic acids, and the like. These buffers can be used singly or in a combination of two or more. Examples of phosphoric acid buffers include phosphoric acid or phosphoric acid salts such as alkali metal phosphate and alkaline earth metal phosphate. Examples of carbonic acid buffers include carbonic acid or carbonic acid salts such as alkali metal carbonate and alkaline earth metal carbonate. Examples of citric acid buffers include citric acid or alkali metal citrate, alkaline earth metal citrate, and the like. As the phosphoric acid buffer, a hydrate of phosphoric acid salt can also be used. More specifically, examples of the phosphoric acid buffer include phosphoric acid or salts thereof (disodium hydrogen phosphate, sodium dihydrogen phosphate, potassium dihydrogen phosphate, trisodium phosphate, dipotassium phosphate, calcium monohydrogen phosphate, calcium dihydrogenphosphate, etc.); examples of the carbonic acid buffer include carbonic acid or salts thereof (sodium bicarbonate, sodium carbonate, ammonium carbonate, potassium carbonate, calcium carbonate, potassium bicarbonate, magnesium carbonate, etc.); examples of the citric acid buffer include citric acid or salts thereof (sodium citrate, potassium citrate, calcium citrate, sodium dihydrogen citrate, disodium citrate, etc.); examples of the acetic acid buffer include acetic acid or salts thereof (ammonium acetate, potassium acetate, calcium acetate, sodium acetate, etc.); aspartic acid or salts thereof (sodium aspartate, magnesium aspartate, potassium aspartate, etc.), and the like. Of these buffers, phosphoric acid buffers (combination of disodium hydrogen phosphate and sodium dihydrogenphosphate) are preferable.

The aqueous ophthalmic composition of the present invention may further include a tonicity agent. The tonicity agent that can be added to the aqueous ophthalmic composition of the present invention is not particularly limited as long as it is a pharmacologically (pharmaceutically) or physiologically acceptable tonicity agent in the field of medicine. Examples of the tonicity agent include disodium hydrogenphosphate, sodium dihydrogenphosphate, potassium dihydrogen phosphate, sodium hydrogen sulfite, sodium sulfite, potassium chloride, calcium chloride, sodium chloride, magnesium chloride, potassium acetate, sodium acetate, sodium bicarbonate, sodium carbonate, sodium tiosulfate, magnesium sulfate, glycerin, propylene glycol, polyethylene glycol, glucose, mannitol, sorbitol, and the like. These tonicity agents can be used singly or in a combination of two or more.

As a tonicity agent that can be added to the aqueous ophthalmic composition of the present invention, polyhydric alcohol is preferable, and examples thereof include glycerin, propylene glycol, polyethylene glycol, mannitol, sorbitol, and the like. Glycerin and propylene glycol are more preferable, and glycerin is particularly preferable.

When a tonicity agent is added to the aqueous ophthalmic composition of the present invention, the content thereof is suitably determined according to the kind of the tonicity agent, kinds and contents of other components, and the application, preparation form, usage, etc. of the aqueous ophthalmic composition. For example, the total content of the tonicity agent is 0.005 to 10 w/v %, preferably 0.01 to 5 w/v %, and more preferably 0.05 to 3 w/v % based on the total amount of the aqueous ophthalmic composition of the present invention.

The pH of the aqueous ophthalmic composition is not particularly limited as long as it is within a pharmacologically (pharmaceutically) or physiologically acceptable range in the field of medicine. For example, the pH of the aqueous ophthalmic composition of the present invention is in the range of 4.0 to 9.5, preferably 5.0 to 9.0, and more preferably 5.5 to 8.5.

The osmotic pressure of the aqueous ophthalmic composition of the present invention is not particularly limited as long as it is within a range acceptable to the human body. For example, the osmotic pressure ratio of the aqueous ophthalmic composition of the present invention is 0.5 to 5.0, preferably 0.6 to 3.0, more preferably 0.7 to 2.0, and particularly preferably 0.9 to 1.55. The osmotic pressure is adjusted using an inorganic salt, polyhydric alcohol, sugar alcohol, sugar, etc., according to a known method in the technical field of the present invention. The osmotic pressure ratio is the ratio of the osmotic pressure of a sample to 286 mOsm (osmotic pressure of 0.9 w/v % aqueous sodium chloride solution) based on the Japanese Pharmacopoeia, 16th revision, and can be measured with reference to the osmotic measurement method (freezing point depression method) described in the Japanese Pharmacopoeia. The reference solution for measuring the ratio of osmotic pressure (0.9 w/v % sodium chloride solution), after sodium chloride (standard reagent according to the Japanese Pharmacopoeia is dried for 40 to 50 minutes at 500 to 650° C., the sodium chloride is allowed to cool in a desiccator (silica gel), and 0.900 g of the resultant is accurately measured. The resultant is then dissolved in purified water, thus preparing 100 mL of the solution with accuracy. Alternatively, a commercially available reference solution for measuring the osmotic pressure ratio (0.9 w/v % sodium chloride solution) can be used.

The viscosity of the aqueous ophthalmic composition of the present invention is not particularly limited as long as it is within a range acceptable to the human body. For example, the viscosity at 25° C., which is measured by a rotation viscometer (RE550 type viscosity meter, produced by Toki Sangyo Co., Ltd., rotor: 1° 34'×24) is 0.01 to 1,000 mPa·s, preferably 0.05 to 100 mPa·s, and more preferably 0.1 to 10 mPa·s.

As long as the aqueous ophthalmic composition of the present invention attains the effect of the present invention, it may contain, in addition to the aforementioned components, a suitable amount of various pharmacologically active components and/or biologically active components singly or in a combination. Such components are not particularly limited, and examples of the specific components used in an ophthalmological drug are as follows:

antihistamines or antiallergic agents such as iproheptine, diphenhydramine hydrochloride, chlorphenylamine maleate, ketotifen fumarate, pemirolast potassium, and sodium cromoglycate;

decongestants such as tetrahydrozoline hydrochloride, naphazoline hydrochloride, naphazoline sulfate, epinephrine hydrochloride, ephedrine hydrochloride, and methylephedrine hydrochloride;

vitamins such as flavin adenine dinucleotide sodium, cyanocobalamin, retinol acetate, retinol palmitate, pyridoxine hydrochloride, pantenol, calcium pantothenate, and tocopherol acetate;

amino acids such as potassium aspartate, magnesium aspartate, epsilon-aminocaproic acid, and sodium chondroitin sulfate;

antiphlogistics such as bromfenac sodium, dipotassium glycyrrhizate, pranoprofen, allantoin, azulene, sodium azulene sulfonate, guaiazulene, berberine chloride, berberine sulfate, lysozyme chloride, and licorice; and others such as sodium hyaluronate, sulfamethoxazole, and sulfamethoxazole sodium.

Further, in the aqueous ophthalmic composition of the present invention, as long as the effect of the invention is attained, a suitable amount of one or more additives selected from various additives can be suitably added by a conventional method according to the application, preparation form, etc. of the aqueous ophthalmic composition. Typical components include the following additives:

carriers such as water, moisture ethanol, and like aqueous carriers;

sugars such as cyclodextrin;

sugar alcohols such as xylitol, sorbitol, and mannitol, wherein these compounds may be in the d form, l form, or dl form;

antiseptics, disinfectants, and antibacterial agents such as cetyl pyridinium, benzalkonium chloride, benzethonium chloride, polyhexanide hydrochloride, alkyldiaminoethylglycine hydrochloride, sodium benzoate, ethanol, chloro butanol, sorbic acid, potassium sorbate, sodium dehydroacetate, methyl parahydroxybenzoate, ethyl parahydroxybenzoate, propyl parahydroxybenzoate, butyl parahydroxybenzoate, oxyquinoline sulfate, phenethyl alcohol, benzyl alcohol, and Glokill (trade name, Rhodia Co., Ltd.);

thickening agents or thickeners such as powdered Acacia, sodium alginate, propylene glycol alginate, sodium chondroitin sulfate, sorbitol, dextran 70, powdered tragacanth, methylcellulose, carboxymethyl cellulose, hydroxyethyl cellulose, hydroxypropyl methylcellulose, carboxyvinyl polymer, polyvinyl alcohol, polyvinyl pyrrolidone, and macrogol 4000;

oils such as castor oil; and the like.

The aqueous ophthalmic composition of the present invention can be prepared by adding a desired amount of each of component (A) and component (B), and if necessary, other components to a carrier so that the aqueous ophthalmic composition has a desired concentration. For example, eye drops, solutions for wearing a contact lens, eye washes, or contact lens care solutions are prepared by dissolving or suspending the aforementioned components in purified water, adjusting the pH and osmotic pressure to the predetermined levels, and subjecting these to sterilization treatment by filter sterilization, etc. Regarding the dissolution of components (A) and (B), and the dissolution of components with a high hydrophobic property, components having a solubilizing action such as surfactants may be added beforehand, then the mixture is stirred, after which purified water is added thereto, followed by dissolution or suspension.

Accordingly, from a different viewpoint, the present invention provides a method for producing an aqueous ophthalmic composition comprising adding (A) polyoxyethylene castor oil and (B) sesame oil to a water-containing carrier.

The aqueous ophthalmic composition of the present invention indicates an ophthalmic composition in which the amount of water exceeds 85 w/v % or more based on the total amount of the aqueous ophthalmic composition. The content of water in the aqueous ophthalmic composition is preferably 90 w/v % or more, more preferably 92 w/v % or more, even more preferably 94 w/v % or more, and particularly more preferably 96 w/v % or more. As the water used in the aqueous ophthalmic composition of the present invention, pharmacologically (pharmaceutically) or physiologically acceptable water in the field of medicine can be used. Examples of water include distilled water, water, purified water, sterile purified water, water for injection, distilled water for injection, and the like. The dosage form of the aqueous ophthalmic composition is not particularly limited as long as it can be used in the field of ophthalmology. The dosage form is preferably liquid. These definitions are based on the Japanese Pharmacopoeia, $16^{th}$ revision.

Examples of the aqueous ophthalmic composition of the present invention include eye drops (also called as ophthalmic solutions or ophthalmic drugs) [note that examples of the eye drops include artificial tears and ophthalmic agents that can be instilled into eyes during use of contact lenses,] eye washes (also referred to as collyriums or eye lotions) [note that examples of eye washes include eye washes that can wash eyes during use of contact lenses,] solutions for wearing a contact lens, contact lens care products, (disinfectant solutions for contact lenses, storage solutions for contact lenses, cleansing solutions for contact lenses, cleansing and storage solutions for contact lenses, disinfectant, storage, and cleansing solutions for contact lenses (multiple-purpose solutions for contact lenses), etc. The aqueous ophthalmic composition of the present invention ensures a reduced defoaming time, and low variation in the drip amount during use. Therefore, the present invention is preferably used in eye drops and solutions for wearing contact lenses that are used in a particularly small amount each time compared to other dosage forms. The present invention is particularly preferably used in eye drops.

Because the preservative efficacy of the aqueous ophthalmic composition of the present invention is enhanced, the composition has excellent antiseptic effect even without containing a known antiseptic such as chlorhexidine. For this reason, the present invention is preferably used as a multidose aqueous ophthalmic composition, i.e., an aqueous ophthalmic composition, which is used more than once after the product is opened. The aqueous ophthalmic composition can be stably stored for a few days or a few weeks or longer.

Further, in addition to a reduced deforming time and enhanced preservative efficacy, the aqueous ophthalmic composition of the present invention has improved photostability. For this reason, the aqueous ophthalmic composition of the present invention can stably exhibit original properties of polyoxyethylene castor oil as a surfactant. Therefore, the aqueous ophthalmic composition of the present invention is preferably used as an aqueous ophthalmic composition that requires a sufficient cleansing effect compared to other dosage forms. From this point of view, the aqueous ophthalmic composition of the present invention is particularly preferably used as an eye wash.

As the container that holds the aqueous ophthalmic composition of the present invention, a container that can be generally used to hold an aqueous ophthalmic composition can be used. The container may be made of glass or plastic. When a plastic container is used to hold the aqueous ophthalmic composition of the present invention, although constituent materials of the plastic container are not particularly limited, polyethylenenaphthalate, polyarylate, polyethylene terephthalate, polypropylene, polyethylene, and polyimide can be used alone or in a mixture of two or more. The copolymers thereof can also be used. Examples of the copolymers include copolymers that contain other polyester units or imide units, in addition to any one of ethylene-2,6-naphthalate units, arylate units, ethylene terephthalate units, propylene units, ethylene units, and imide units, which is contained as a main component. In the present invention, for example, a polyethylene terephthalate container indicates a container in which polyethylene terephthalate is contained in an amount of 50 w/w % or more based on the weight of the total weight of the constituent materials of the container.

The structure, constituent materials, etc., of a container spout periphery such as a nozzle mounted on a container containing the aqueous ophthalmic composition of the present invention is not particularly limited. The structure of the container spout periphery such as a nozzle may be a generally applicable structure as a spout (e.g., nozzle) of a container for ophthalmologic compositions (e.g., container for eye drops), and the nozzle may be integrally or separately formed with the container. Examples of the constituent materials of the spout periphery or spout (e.g., nozzle) include those mentioned in the constituent materials of the plastic containers.

In particular, to further improve flexibility, cost, and/or an effect of reducing variation in the drip amount, a spout that contains polyethylene or polypropylene as a constituent material is preferable. Examples of polyethylene include high-density polyethylene, low-density polyethylene, and the like; particularly, of these, a spout containing low-density polyethylene as a constituent material is preferable. As a spout, a nozzle used for a container of eye drops is preferable.

As a preferable combination of a container that holds the aqueous ophthalmic composition of the present invention and a container spout periphery, it is possible to use a combination of a polyethylene terephthalate container and a polyethylene container spout periphery, more preferably, a combination of a polyethylene terephthalate eye drop container and a polyethylene nozzle, and particularly more preferably, a combination of a polyethylene terephthalate eye drop container and a low-density polyethylene nozzle. Such a combination can significantly exhibit the effect of reducing variation in the drip amount in the present invention.

Since the aqueous ophthalmic composition of the present invention can reduce the defoaming time, reduce variation in the drip amount during use, and can be instilled into an eye in a specific amount per use, it is particularly suitably used as eye drops containing a pharmacologically active component and/or a biologically active component. Such eye drops can be used as eye drops for dry eyes, decongestant eye drops, antibacterial eye drops, anti-inflammatory eye drops, eye drops for relieving itchy eyes, eye drops for relieving eye strain, etc.

From a different viewpoint, the present invention also provides use of (A) polyoxyethylene castor oil and (B) sesame oil, for the production of an aqueous ophthalmic composition.

From another different viewpoint, the present invention also provides use of a composition as an aqueous ophthalmic composition, the composition comprising (A) polyoxyethylene castor oil and (B) sesame oil.

From still another different viewpoint, the present invention provides a composition for use as an aqueous ophthalmic composition, the composition comprising (A) polyoxyethylene castor oil and (B) sesame oil.

2. Method for Reducing Defoaming Time

As mentioned above, in the aqueous ophthalmic composition of the present invention, by containing component (A) and component (B), the defoaming time can be reduced in the aqueous ophthalmic composition; consequently, variation in the drip amount during use can be reduced.

Therefore, from a different viewpoint, the present invention provides a method for reducing the defoaming time in an aqueous ophthalmic composition, comprising adding (A) polyoxyethylene castor oil and (B) sesame oil to the aqueous ophthalmic composition.

The present invention also provides a method for reducing the defoaming time of an aqueous ophthalmic composition, comprising adding (B) sesame oil to the aqueous ophthalmic composition containing (A) polyoxyethylene castor oil.

The present invention provides a method for reducing variation in the drip amount during use of an aqueous ophthalmic composition, comprising adding (A) polyoxyethylene castor oil and (B) sesame oil to the aqueous ophthalmic composition.

In these methods, as long as component (A) and component (B) are both present, they may be added at the same time or separately, and the order thereof is not particularly limited. The kinds of component (A) and component (B) to be used, the contents (or addition contents) and the ratio thereof, the kinds and contents (addition contents) of components added other than the above, the preparation form of the aqueous ophthalmic composition, the kind and the combination of the container, the embodiment method, and the like are the same as in the "1. Aqueous Ophthalmic Composition" section above.

In particular, the methods described above are suitably used when the aqueous ophthalmic composition is used as eye drops or a solution for wearing a contact lens.

In the present specification, whether the defoaming time in the aqueous ophthalmic composition is shortened or not can be determined according to the method in the Examples described below.

3. Method for Enhancing Preservative Efficacy

As described above, the preservative efficacy can be significantly enhanced in the aqueous ophthalmic composition by containing component (A) and component (B).

Accordingly, from another viewpoint, the present invention provides a method for enhancing the preservative efficacy in the aqueous ophthalmic composition, comprising adding (A) polyoxyethylene castor oil and (B) sesame oil to the aqueous ophthalmic composition.

In this method, as long as component (A) and component (B) are both present, they may be added at the same time or separately, and the order thereof is not particularly limited. The kinds, contents (or addition contents), and the ratio of component (A) and component (B), the kinds and contents (addition contents) of components added other than the above, the preparation form of the aqueous ophthalmic composition, the kind and the combination of the container, the embodiment method, and the like, are the same as in the "1. Aqueous Ophthalmic Composition" section above.

Of these methods, the aqueous ophthalmic composition is preferably used as a multidose aqueous ophthalmic composition, i.e., an aqueous ophthalmic composition used more than one time after the product is opened. Examples of such an aqueous ophthalmic composition include multidose eye drops, multidose eye washes, multidose solutions for wearing a contact lens, and multidose contact lens care products.

In the present specification, whether the preservative efficacy in the aqueous ophthalmic composition is enhanced or not can be determined according to the method in the Examples described below.

4. Photostabilization Method

As described above, by adding (B) sesame oil together with (A) polyoxyethylene castor oil to the aqueous ophthalmic composition, photodecomposition of the polyoxyethylene castor oil contained in the aqueous ophthalmic composition can be inhibited.

Accordingly, the present invention provides a method for improving photostability in an aqueous ophthalmic composition containing (A) polyoxyethylene castor oil, comprising adding (B) castor oil to the aqueous ophthalmic composition.

Further, the present invention also provides a method for improving photostability in the aqueous ophthalmic composition, comprising adding (A) polyoxyethylene castor oil and (B) castor oil to the aqueous ophthalmic composition.

In these methods, as long as component (A) and component (B) are both present in the aqueous ophthalmic composition, the addition order thereof is not particularly limited. The kinds, contents, and ratio of components (A) and (B), the kinds and contents of components added other than the above, and the preparation form of the composition are the same as those of the aqueous ophthalmic composition of the present invention.

In the present specification, whether the photostability in the aqueous ophthalmic composition is improved or not can be determined according to the method described in the Examples below.

EXAMPLES

Examples and Test Examples are given below to illustrate the present invention in detail; however, the present invention is not limited to these Examples and the like.

Test Example 1

Defoaming Time Test (1)

Aqueous ophthalmic compositions having the formulations shown in the following Tables 1 to 3 were prepared by a standard method, and defoaming times were evaluated using these compositions. Polyoxyethylene castor oil 10 that conforms to the standard for polyoxyethylene castor oil in Japanese Pharmaceutical Excipients 2003 and in which the average number of moles of added ethylene oxide is 10 was used, and sesame oil manufactured by Sigma was used.

Subsequently, each of the aqueous ophthalmic compositions in an amount of 30 mL was placed in individual 50-mL glass centrifuge tubes, and the tubes were shaken 1,500 times using a Recipad Shaker SR-2w (TAITEC). Immediately after shaking, a foam part and an aqueous solution part were confirmed by visual observation, and the volume of the foam part was measured. Thereafter, the tubes were allowed to stand, the volume of the foam part was measured over time, and the time required for the foam to completely disappear was measured.

Based on the defoaming time of each control and the defoaming time of each Example, reduction rates in defoaming time due to the sesame oil were calculated with the following formula. A larger reduction rate means a higher foam disappearance speed.

Reduction rate in defoaming time(%)=(defoaming time of corresponding control−defoaming time of each Example)/(defoaming time of corresponding control)×100

The corresponding controls are, specifically, Control 1 for Examples 1-1 and 1-2, Control 2 for Examples 2-1 and 2-2, Control 3 for Examples 3-1 and 3-2, Control 4 for Examples 4-1 and 4-2, Control 5 for Examples 5-1 and 5-2, and Control 6 for Examples 6-1 and 6-2. The results are also shown in Tables 1 to 3.

TABLE 1

Unit: w/v %

| | Control 1 | Control 2 | Control 3 | Control 4 | Control 5 | Control 6 |
|---|---|---|---|---|---|---|
| Polyoxyethylene castor oil 10 | 0.05 | 0.1 | 0.2 | 0.3 | 0.4 | 0.5 |
| Glycerin | 2.5 | 2.5 | 2.5 | 2.5 | 2.5 | 2.5 |
| Boric acid | 0.5 | 0.5 | 0.5 | 0.5 | 0.5 | 0.5 |
| Borax | 0.2 | 0.2 | 0.2 | 0.2 | 0.2 | 0.2 |
| Purified water | Balance | Balance | Balance | Balance | Balance | Balance |
| pH | 7.0 | 7.0 | 7.0 | 7.0 | 7.0 | 7.0 |

TABLE 2

Unit: w/v %

| | Example 1-1 | Example 2-1 | Example 3-1 | Example 4-1 | Example 5-1 | Example 6-1 |
|---|---|---|---|---|---|---|
| Polyoxyethylene castor oil 10 | 0.05 | 0.1 | 0.2 | 0.3 | 0.4 | 0.5 |
| Glycerin | 2.5 | 2.5 | 2.5 | 2.5 | 2.5 | 2.5 |
| Sesame oil | 0.01 | 0.01 | 0.01 | 0.01 | 0.01 | 0.01 |
| Boric acid | 0.5 | 0.5 | 0.5 | 0.5 | 0.5 | 0.5 |
| Borax | 0.2 | 0.2 | 0.2 | 0.2 | 0.2 | 0.2 |
| Purified water | Balance | Balance | Balance | Balance | Balance | Balance |
| pH | 7.0 | 7.0 | 7.0 | 7.0 | 7.0 | 7.0 |

TABLE 2-continued

Unit: w/v %

|  | Example 1-1 | Example 2-1 | Example 3-1 | Example 4-1 | Example 5-1 | Example 6-1 |
|---|---|---|---|---|---|---|
| Reduction rate in defoaming time (%) | 98 | 91 | 60 | 79 | 86 | 70 |

TABLE 3

Unit: w/v %

|  | Example 1-2 | Example 2-2 | Example 3-2 | Example 4-2 | Example 5-2 | Example 6-2 |
|---|---|---|---|---|---|---|
| Polyoxyethylene castor oil 10 | 0.05 | 0.1 | 0.2 | 0.3 | 0.4 | 0.5 |
| Glycerin | 2.5 | 2.5 | 2.5 | 2.5 | 2.5 | 2.5 |
| Sesame oil | 0.05 | 0.05 | 0.05 | 0.05 | 0.05 | 0.05 |
| Boric acid | 0.5 | 0.5 | 0.5 | 0.5 | 0.5 | 0.5 |
| Borax | 0.2 | 0.2 | 0.2 | 0.2 | 0.2 | 0.2 |
| Purified water | Balance | Balance | Balance | Balance | Balance | Balance |
| pH | 7.0 | 7.0 | 7.0 | 7.0 | 7.0 | 7.0 |
| Reduction rate in defoaming time (%) | 66 | 91 | 98 | 95 | 97 | 97 |

As shown in Tables 1 to 3, it was confirmed that the defoaming times were significantly reduced in the aqueous ophthalmic compositions containing the polyoxyethylene castor oil 10 at various concentrations and containing the sesame oil (Examples 1-1 to 6-2), as compared to the aqueous ophthalmic compositions containing the polyoxyethylene castor oil 10 but not containing the sesame oil (Controls 1 to 6).

Test Example 2

Defoaming Time Test (2)

Aqueous ophthalmic compositions having the formulations shown in the following Tables 4 and 5 were prepared by a standard method, and defoaming times were evaluated. Polyoxyethylene castor oil 35 that conforms to the standard for polyoxyethylene castor oil in Japanese Pharmaceutical Excipients 2003 and in which the average number of moles of added ethylene oxide is 35 was used, and the same sesame oil as in Test Example 1 was used.

Using these aqueous ophthalmic compositions, reduction rates in defoaming time due to the sesame oil were calculated with the following formula in the same manner as in Test Example 1. Since the defoaming times were longer than those in Test Example 1, the time required for the initial foam to be reduced by half was evaluated as the foam half-volume period, and reduction rates thereof were calculated with the following formula. A larger reduction rate means a higher foam disappearance speed.

Reduction rate in foam half-volume period(%)=(foam half-volume period of corresponding control−foam half-volume period of each Example)/(foam half-volume period of corresponding control)×100

The corresponding controls are, specifically, Control 7 for Example 7, Control 8 for Example 8, and Control 9 for Example 9. The results are also shown in Tables 4 and 5.

TABLE 4

Unit: w/v %

|  | Control 7 | Control 8 | Control 9 |
|---|---|---|---|
| Polyoxyethylene castor oil 35 | 0.05 | 0.3 | 0.5 |
| Glycerin | 2.5 | 2.5 | 2.5 |
| Boric acid | 0.5 | 0.5 | 0.5 |
| Borax | 0.1 | 0.2 | 0.2 |
| Purified water | Balance | Balance | Balance |
| pH | 7.0 | 7.0 | 7.0 |

TABLE 5

Unit: w/v %

|  | Example 7 | Example 8 | Example 9 |
|---|---|---|---|
| Polyoxyethylene castor oil 35 | 0.05 | 0.3 | 0.5 |
| Glycerin | 2.5 | 2.5 | 2.5 |
| Sesame oil | 0.05 | 0.05 | 0.05 |
| Boric acid | 0.5 | 0.5 | 0.5 |
| Borax | 0.2 | 0.2 | 0.1 |
| Purified water | Balance | Balance | Balance |
| pH | 7.0 | 7.0 | 7.0 |
| Reduction rate in foam half-volume period (%) | 74 | 42 | 58 |

As shown in Tables 4 and 5, it was confirmed that the foam half-volume periods were significantly reduced in the aqueous ophthalmic compositions containing the polyoxyethylene castor oil 35 at various concentrations and containing the sesame oil (Examples 7 to 9), as compared to the aqueous ophthalmic compositions containing the polyoxyethylene castor oil 35 but not containing the sesame oil (Controls 7 to 9).

Test Example 3

Defoaming Time Test (3)

Aqueous ophthalmic compositions having the formulations shown in the following Tables 6 and 7 were prepared by a standard method, and defoaming times were evaluated. The same polyoxyethylene castor oil 35 as in Test Example 2 was used, and castor oil manufactured by Wako was used. In the table, vitamin A oil containing 55 weight % retinol palmitate, which is vitamin A, and 45 weight % sunflower oil was used. The vitamin A oil was in an amount of 1,000,000 IU/g in terms of IU, which is an international unit for the amount of vitamin A.

Using these aqueous ophthalmic compositions, reduction rates in foam half-volume period were calculated from the following formula in the same manner as in Test Example 2.

Reduction rate in foam half-volume period(%)=(foam half-volume period of corresponding control−foam half-volume period of each Comparative Example)/(foam half-volume period of corresponding control)×100

The corresponding controls are, specifically, Control 10 for Comparative Example 1, Control 11 for Comparative Example 2, and Control 12 for Comparative Examples 3 and 4. The results are also shown in Tables 6 and 7.

TABLE 6

Unit: w/v %

|  | Control 10 | Control 11 | Control 12 |
| --- | --- | --- | --- |
| Polyoxyethylene castor oil 35 | 0.05 | 0.3 | 0.5 |
| Glycerin | 2.5 | 2.5 | 2.5 |
| Boric acid | 0.5 | 0.5 | 0.5 |
| Borax | 0.1 | 0.2 | 0.2 |
| Purified water | Balance | Balance | Balance |
| pH | 7.0 | 7.0 | 7.0 |

TABLE 7

Unit: w/v %

|  | Comparative Example 1 | Comparative Example 2 | Comparative Example 3 | Comparative Example 4 |
| --- | --- | --- | --- | --- |
| Polyoxyethylene castor oil 35 | 0.05 | 0.3 | 0.5 | 0.5 |
| Glycerin | 2.5 | 2.5 | 2.5 | 2.5 |
| Castor oil | 0.01 | 0.01 | 0.01 | — |
| Vitamin A oil (1,000,000 IU/g) | — | — | — | 0.01 (10,000 IU) |
| Boric acid | 0.5 | 0.5 | 0.5 | 0.5 |
| Borax | 0.2 | 0.2 | 0.2 | 0.2 |
| Purified water | Balance | Balance | Balance | Balance |
| pH | 7.0 | 7.0 | 7.0 | 7.0 |
| Reduction rate in foam half-volume period (%) | 0 | 0 | −120 | 0 |

Note:
The figure in parentheses indicates the amount of vitamin A contained in 100 mL of the composition.

As shown in Tables 6 and 7, in the aqueous ophthalmic compositions containing the polyoxyethylene castor oil 35 at various concentrations and containing the castor oil or the vitamin A oil (Comparative Examples 1 to 4), the foam half-volume periods were similar to those of the aqueous ophthalmic compositions containing the polyoxyethylene castor oil 35 but containing neither the castor oil nor the vitamin A oil (Controls 10 to 12), or were extended as compared to the controls, with no reduction effect on the defoaming time being observed.

Test Example 4

Preservative Efficacy Test

Aqueous ophthalmic compositions shown in the following Table 8 were prepared according to a standard method, and a preservative efficacy test was performed by the following method for each of the aqueous ophthalmic compositions. The same polyoxyethylene castor oil 10 and sesame oil as in Test Example 1 were used.

*Staphylococcus aureus* (ATCC6538) was inoculated on the surface of a soybean-casein digest slant medium and cultured at 33° C. for 24 hours. The cultured cells were aseptically collected using a platinum loop and suspended in an appropriate amount of sterile physiological saline to prepare a bacterial suspension containing viable cells at about $1 \times 10^6$ CFU/mL. The viable cell count in the suspension was measured by culturing separately. Subsequently, the aqueous ophthalmic compositions were filter-sterilized, and each of the aqueous ophthalmic compositions in an amount of 5 mL was placed in individual 15-mL Corning conical tubes (PET). The *Staphylococcus aureus* bacterial suspension (suspended in physiological saline) was inoculated into each of the aqueous ophthalmic compositions so that the viable cell count (final concentration) was about $10^4$ CFU/mL, and stirred thoroughly to prepare samples. The samples were stored at 23° C. for 48 hours while shielded from light. After this 48-hour-period ended, each of the samples containing viable cells was adjusted to have an adequate concentration for counting, seeded in a soybean-casein digest agar medium (SCDLP agar medium) containing lecithin and polysorbate 80, and cultured overnight at 33° C. Thereafter, the number of observed colonies was counted to determine the viable cell count for each of the samples. The results are also shown in Table 8.

TABLE 8

Unit: w/v %

|  | Comparative Example 5 | Comparative Example 6 | Comparative Example 7 | Comparative Example 8 | Example 10 | Example 11 |
|---|---|---|---|---|---|---|
| Polyoxyethylene castor oil 10 | — | 0.2 | 0.5 | — | 0.2 | 0.5 |
| Sesame oil | — | — | — | 0.05 | 0.05 | 0.05 |
| Glycerin | 2.5 | 2.5 | 2.5 | 2.5 | 2.5 | 2.5 |
| Polysorbate 80 | 0.2 | 0.2 | 0.2 | 0.2 | 0.2 | 0.2 |
| Boric acid | 0.5 | 0.5 | 0.5 | 0.5 | 0.5 | 0.5 |
| Borax | 0.2 | 0.2 | 0.2 | 0.2 | 0.2 | 0.2 |
| Purified water | Balance | Balance | Balance | Balance | Balance | Balance |
| pH | 7.0 | 7.0 | 8.0 | 7.0 | 7.0 | 7.0 |
| Viable cell count after 48 hours | 620 | 630 | 120 | 6420 | 80 | 100 |

As shown in Table 8, compared to the aqueous ophthalmic composition of Comparative Example 5 (containing neither the polyoxyethylene castor oil 10 nor the sesame oil), the viable cell count of the aqueous ophthalmic composition of Comparative Example 6 (containing the polyoxyethylene castor oil 10) was almost unchanged, and the viable cell count of the aqueous ophthalmic composition of Comparative Example 7 decreased to 120. However, the viable cell count after 48 hours was larger in the aqueous ophthalmic composition of Comparative Example 8 (containing the sesame oil) than in the aqueous ophthalmic composition of Comparative Example 5, indicating that the sesame oil alone does not have action of enhancing preservative efficacy, but rather delays decrease in viable cells. In contrast, decrease in viable cells was accelerated in the aqueous ophthalmic compositions of Examples 10 and 11 (containing the polyoxyethylene castor oil 10 and the sesame oil), as compared to the aqueous ophthalmic compositions of Comparative Examples 6 and 7. From these results, it was confirmed that preservative efficacy is enhanced when polyoxyethylene castor oil 10 and sesame oil are contained.

Test Example 5

Photostability Test

Aqueous ophthalmic compositions having the formulations shown in the following Table 9 were prepared by a standard method, and photostability was evaluated. The same polyoxyethylene castor oil 10 and sesame oil as in Test Example 1 were used.

Subsequently, each of the prepared aqueous ophthalmic compositions in an amount of 5 mL was placed in individual 10-mL glass screw vials. Each of the aqueous ophthalmic compositions was continuously irradiated with a light of 5,000 lx for 120 hours at room temperature by using a photostability testing device (Light-Tron LT-120 D3CJ manufactured by Nagano Science) with a D65 lamp as a light source to be exposed to a light with a cumulative irradiation amount of 600,000 lx·hr. After the light exposure, the content of the polyoxyethylene castor oil 10 in each of the aqueous ophthalmic compositions was quantified using HPLC to calculate the residual rate of the polyoxyethylene castor oil 10 according to the following formula.

Residual rate(%)=(content of polyoxyethylene castor oil 10 after light irradiation)/(content of polyoxyethylene castor oil 10 before light irradiation)×100

Further, the photostability improvement rate (%) was calculated using the following formula. The results are also shown in Table 9.

Photostability improvement rate(%)={(residual rate of Example 12/residual rate of Comparative Example 9)−1}×100

TABLE 9

Unit: w/v %

|  | Comparative Example 9 | Example 12 |
|---|---|---|
| Polyoxyethylene castor oil 10 | 0.2 | 0.2 |
| Sesame oil | — | 0.05 |
| Polysorbate 80 | 0.2 | 0.2 |
| Boric acid | 0.5 | 0.5 |
| Borax | 0.03 | 0.03 |
| Purified water | Balance | Balance |
| pH | 7.0 | 7.0 |
| Photostability improvement rate (%) | — | 30.0 |

As shown in Table 9, it was confirmed that as compared to the aqueous ophthalmic composition containing the polyoxyethylene castor oil 10 (Comparative Example 9), the residual rate of the polyoxyethylene castor oil 10 was significantly improved and the photostability improvement rate of the polyoxyethylene castor oil 10 was increased in the aqueous ophthalmic composition containing the polyoxyethylene castor oil 10 and the sesame oil (Example 12).

These results show that aqueous ophthalmic compositions containing polyoxyethylene castor oil and sesame oil allow the properties of polyoxyethylene castor oil, which is a nonionic surfactant, to be stably exhibited for a long period of time and are suitable for applications such as eye washes.

Test Example 6

Preservative Efficacy Test (2)

Aqueous ophthalmic compositions shown in the following Table 10 were prepared by a standard method, and a preservative efficacy test was conducted by the following method for each of the aqueous ophthalmic compositions. The same polyoxyethylene castor oil 35 and sesame oil as in Test Examples 1 and 2 were used.

Using each of the aqueous ophthalmic compositions, the viable cell count was determined by the same method as in Test Example 4. The results are also shown in Table 10.

TABLE 10

Unit: w/v %

|  | Comparative Example 10 | Comparative Example 11 | Example 13 | Example 14 |
|---|---|---|---|---|
| Polyoxyethylene castor oil 35 | — | 0.05 | 0.05 | 0.2 |
| Sesame oil | — | — | 0.05 | 0.05 |
| Glycerin | 2.5 | 2.5 | 2.5 | 2.5 |
| Polysorbate 80 | 0.2 | 0.2 | 0.2 | 0.2 |
| Boric acid | 0.5 | 0.5 | 0.5 | 0.5 |
| Borax | 0.2 | 0.2 | 0.2 | 0.2 |
| Purified water | Balance | Balance | Balance | Balance |
| pH | 7.0 | 7.0 | 7.0 | 7.0 |
| Viable cell count after 48 hours | 1310 | 4700 | 1070 | 20 |

As shown in Table 10, the viable cell count after 48 hours was larger in the aqueous ophthalmic composition of Comparative Example 11 (containing the polyoxyethylene castor oil 35) than in the aqueous ophthalmic composition of Comparative Example 10 (containing neither the polyoxyethylene castor oil 35 nor the sesame oil), indicating that the polyoxyethylene castor oil 35 alone does not have action of enhancing preservative efficacy, but rather delays decrease in viable cells. In contrast, decrease in viable cells was accelerated in the aqueous ophthalmic compositions of Examples 13 and 14 (containing the polyoxyethylene castor oil 35 and the sesame oil), as compared to the aqueous ophthalmic composition of Comparative Example 10. From these results, it was confirmed that preservative efficacy is enhanced when polyoxyethylene castor oil 35 and sesame oil are contained.

PREPARATION EXAMPLES

According to the formulations shown in Tables 11 and 12, eye drops (Preparation Examples 1 to 8), eye washes (Preparation Examples 9 and 10), and eye drop for soft contact lenses (Preparation Example 11) are prepared.

TABLE 11

Unit: w/v %

|  | Preparation Example 1 Eye drops | Preparation Example 2 Eye drops | Preparation Example 3 Eye drops | Preparation Example 4 Eye drops | Preparation Example 5 Eye drops | Preparation Example 6 Eye drops |
|---|---|---|---|---|---|---|
| Polyoxyethylene castor oil 3 | — | — | — | 0.5 | — | 0.1 |
| Polyoxyethylene castor oil 10 | 0.1 | 0.5 | 0.4 | — | 0.5 | 0.3 |
| Polyoxyethylene castor oil 35 | — | 0.5 | 0.5 | 0.001 | — | 0.2 |
| Sesame oil | 0.1 | 0.0025 | 0.05 | 0.05 | 0.1 | 0.05 |
| Epsilon-aminocaproic acid | — | — | — | 3 | — | — |
| Berberine sulfate hydrate | 0.05 | 0.05 | — | 0.01 | 0.01 | — |
| Sodium azulene sulfonate hydrate | 0.02 | — | 0.01 | — | — | — |
| Chlorpheniramine maleate | 0.03 | — | — | — | 0.03 | 0.015 |
| Pyridoxine hydrochloride | — | 0.1 | — | — | — | — |
| Potassium L-aspartate | 1 | 1 | — | 0.05 | 0.5 | — |
| Aminoethylsulfonic acid | 1 | 0.05 | — | 0.1 | 0.5 | 1 |
| Sodium chondroitin sulfate | — | 0.2 | 0.1 | — | — | — |
| Potassium chloride | — | 0.15 | — | — | 0.04 | 0.08 |
| Calcium chloride | — | — | — | — | — | 0.02 |
| Sodium chloride | 0.1 | 0.3 | — | — | 0.2 | 0.4 |
| Sodium hydrogen phosphate | — | — | 1.2 | — | — | — |
| Sodium dihydrogen phosphate | — | — | 0.22 | — | — | — |
| Glucose | — | — | 0.2 | — | — | 0.1 |
| Boric acid | 0.4 | 1.2 | — | 0.6 | 1 | 0.5 |
| Borax | 0.1 | 0.3 | — | 0.1 | 0.25 | 0.1 |
| l-menthol | 0.03 | 0.004 | — | 0.008 | 0.005 | — |
| d-camphor | — | — | 0.005 | 0.002 | 0.003 | — |
| d-borneol | — | — | 0.001 | — | 0.005 | — |
| Geraniol | 0.003 | — | — | — | — | — |
| Eucalyptus oil | — | — | — | 0.005 | — | — |
| Bergamot oil | 0.002 | 0.005 | — | — | — | — |
| Cool mint No. 71212 | — | 0.015 | — | — | 0.001 | — |
| Peppermint oil | — | — | — | — | — | 0.001 |
| Mentha oil | — | — | 0.005 | — | — | — |
| Benzalkonium chloride | — | 0.01 | — | — | 0.005 | — |
| Polyhexanide hydrochloride | — | 0.0005 | — | — | — | — |

TABLE 11-continued

Unit: w/v %

| | Preparation Example 1 Eye drops | Preparation Example 2 Eye drops | Preparation Example 3 Eye drops | Preparation Example 4 Eye drops | Preparation Example 5 Eye drops | Preparation Example 6 Eye drops |
|---|---|---|---|---|---|---|
| Methyl parahydroxybenzoate | — | — | — | 0.05 | — | — |
| Ethyl parahydroxybenzoate | — | — | — | 0.026 | — | — |
| Chlorobutanol | 0.05 | — | — | — | — | — |
| Polyoxyethylene hydrogenated castor oil 60 | — | — | — | 0.25 | — | — |
| Polysorbate 80 | 0.3 | — | 0.15 | — | 0.3 | 0.5 |
| Poloxamer 407 | 0.05 | — | — | 0.05 | 0.05 | — |
| Propylene glycol | 0.1 | — | 0.1 | 0.01 | — | — |
| Polyvinylpyrrolidone K25 | — | 0.2 | — | — | 1 | — |
| Hydroxyethyl cellulose | 0.05 | — | 0.1 | — | — | 0.2 |
| Hypromellose | — | 0.1 | — | 0.05 | — | — |
| Sodium hyaluronate | 0.05 | — | — | 0.02 | — | — |
| Concentrated glycerin | 0.2 | — | 0.5 | 0.2 | — | — |
| Trometamol | — | 0.1 | 0.2 | — | — | 0.05 |
| Dibutylhydroxytoluene (BHT) | — | 0.005 | — | — | — | — |
| Sodium edetate | 0.03 | — | — | — | 0.005 | — |
| Hydrochloric acid | q.s. | q.s. | q.s. | q.s. | q.s. | q.s. |
| Sodium hydroxide | q.s. | q.s. | q.s. | q.s. | q.s. | q.s. |
| Purified water | Balance | Balance | Balance | Balance | Balance | Balance |
| pH | 8.5 | 7.0 | 6.2 | 4.5 | 6.0 | 6.8 |

TABLE 12

Unit: w/v %

| | Preparation Example 7 eye drops | Preparation Example 8 eye drops | Preparation Example 9 eye wash | Preparation Example 10 eye wash | Preparation Example 11 eye drops for SCL |
|---|---|---|---|---|---|
| Polyoxyethylene castor oil 10 | — | 0.005 | 0.5 | 0.02 | 0.5 |
| Polyoxyethylene castor oil 35 | 0.3 | 0.5 | 0.1 | — | 0.1 |
| Sesame oil | 0.025 | 0.01 | 0.005 | 0.01 | 0.03 |
| Epsilon-aminocaproic acid | 2 | — | — | — | — |
| Berberine sulfate hydrate | 0.05 | — | — | 0.002 | — |
| Sodium azulene sulfonate hydrate | 0.015 | — | — | — | — |
| Chlorpheniramine maleate | — | — | 0.003 | — | — |
| Pyridoxine hydrochloride | 0.05 | — | 0.01 | — | — |
| Potassium L-aspartate | 1 | — | — | 0.1 | 1 |
| Aminoethylsulfonic acid | — | — | 0.1 | — | — |
| Sodium chondroitin sulfate | 0.5 | — | 0.05 | 0.01 | — |
| Potassium chloride | 0.01 | — | — | 0.08 | 0.08 |
| Calcium chloride | 0.005 | — | — | 0.02 | 0.015 |
| Sodium chloride | — | 0.5 | — | 0.3 | 0.4 |
| Boric acid | 0.5 | — | 1.6 | 0.5 | 0.1 |
| Borax | 0.1 | — | 0.35 | 0.01 | 0.1 |
| l-menthol | 0.004 | 0.002 | 0.0005 | 0.001 | 0.02 |
| d-camphor | — | 0.002 | — | — | 0.0001 |
| dl-borneol | — | 0.005 | — | — | — |
| Geraniol | — | — | 0.005 | 0.001 | — |
| Eucalyptus oil | — | — | — | 0.001 | 0.001 |
| Bergamot oil | — | — | — | — | 0.002 |
| Peppermint oil | — | — | 0.02 | — | — |

TABLE 12-continued

Unit: w/v %

| | Preparation Example 7 eye drops | Preparation Example 8 eye drops | Preparation Example 9 eye wash | Preparation Example 10 eye wash | Preparation Example 11 eye drops for SCL |
|---|---|---|---|---|---|
| Mentha oil | — | 0.01 | — | — | — |
| Potassium sorbate | 0.05 | — | 0.1 | — | — |
| Polyhexanide hydrochloride | 0.0005 | — | — | — | 0.001 |
| Chlorobutanol | — | — | — | 0.2 | 0.4 |
| Polyoxyethylene hydrogenated castor oil 60 | 0.2 | — | — | 0.1 | — |
| Polysorbate 80 | — | 0.1 | 0.1 | 0.3 | — |
| Poloxamer 407 | 0.1 | — | 0.05 | — | 0.05 |
| Hydroxyethyl cellulose | — | — | — | — | 0.1 |
| Hypromellose | 0.2 | — | — | — | — |
| Sodium hyaluronate | — | — | 0.02 | — | — |
| Concentrated glycerin | — | — | — | — | 0.2 |
| Trometamol | — | — | — | 1 | — |
| Dibutylhydroxytoluene (BHT) | 0.005 | — | 0.005 | — | — |
| Sodium citrate | — | 0.5 | 0.5 | — | — |
| Sodium edetate | 0.05 | 0.02 | — | 0.03 | 0.01 |
| Hydrochloric acid | q.s. | q.s. | q.s. | q.s. | q.s. |
| Sodium hydroxide | q.s. | q.s. | q.s. | q.s. | q.s. |
| Purified water | Balance | Balance | Balance | Balance | Balance |
| pH | 5.5 | 7.0 | 7.5 | 6.5 | 6.5 |

The invention claimed is:

1. An aqueous ophthalmic composition comprising (A) polyoxyethylene castor oil and (B) sesame oil, wherein the total content of component (B) is 0.00002 to 10,000 parts by weight relative to 1 part by weight of the total content of component (A).

2. The aqueous ophthalmic composition according to claim 1, which further comprises (C) at least one member selected from the group consisting of boric acids and salts thereof.

3. The aqueous ophthalmic composition according to claim 1, which further comprises at least one member selected from the group consisting of nonionic surfactants other than component (A) and polyhydric alcohols.

4. The aqueous ophthalmic composition according to claim 2, which further comprises at least one member selected from the group consisting of nonionic surfactants other than component (A) and polyhydric alcohols.

5. A method for reducing defoaming time in an aqueous ophthalmic composition, comprising adding (A) polyoxyethylene castor oil and (B) sesame oil, wherein the total content of component (B) is 0.00002 to 10,000 parts by weight relative to 0 part by weight of the total content of component (A), to the aqueous ophthalmic composition.

* * * * *